US00PP27742P3

(12) United States Plant Patent
Grosser

(10) Patent No.: US PP27,742 P3
(45) Date of Patent: Mar. 7, 2017

(54) CITRUS ROOTSTOCK NAMED 'UFR-2'

(50) Latin Name: [***Citrus reticulata*×*Citrus paradisi)*+*Citrus grandis*]×[*Citrus reticulata*+*Poncirus trifoliata* (trifoliate orange)**]
Varietal Denomination: UFR-2

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,423

(22) Filed: Jan. 5, 2015

(65) Prior Publication Data

US 2015/0195973 P1 Jul. 9, 2015

Related U.S. Application Data

(60) Provisional application No. 61/923,587, filed on Jan. 3, 2014.

(51) Int. Cl.
*A01H 5/08* (2006.01)

(52) U.S. Cl.
USPC ..... Plt./201

(58) Field of Classification Search
USPC ..... Plt./201
CPC ..... A01H 5/0806
See application file for complete search history.

(56) References Cited

U.S. PATENT DOCUMENTS

PP21,535 P2 11/2010 Grosser

OTHER PUBLICATIONS

Florida Foundation Seed Producers, Inc.; 9 New Citrus Rootstocks—Descriptions and Data; May 2014, 14 pages.*
U.S. Appl. No. 14/544,424, filed Jan. 5, 2015, Grosser.
U.S. Appl. No. 14/544,425, filed Jan. 5, 2015, Grosser.
U.S. Appl. No. 14/544,427, filed Jan. 5, 2015, Grosser.
U.S. Appl. No. 14/544,572, filed Jan. 22, 2015, Grosser.
U.S. Appl. No. 14/544,571, filed Jan. 22, 2015, Grosser.
U.S. Appl. No. 14/544,573, filed Jan. 22, 2015, Grosser.
U.S. Appl. No. 14/545,063, filed Mar. 20, 2015, Grosser.
U.S. Appl. No. 14/544,570, filed Jan. 22, 2015, Grosser.
Grosser et al., "Protoplast fusion and citrus improvement," *Plant Breeding Reviews* 8:339-374, 1990.
Grosser et al., "Salinity tolerance of 'Valencia' orange trees on allotetraploid rootstocks," *Proc. Fla. State Hort.* 125:50-55, 2012.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora-Diaprepes* Complex via Greenhouse Screening," *Proc. Fla. State Hort. Soc.* 120:103-109, 2007.
Grosser et al., "Protoplast fusion for production of tetraploids and triploids: Applications for scion and rootstock breeding in citrus," *Plant Cell Tissue Organ Culture* 104:343-357, 2011.
Letter and corresponding informational document to Florida citrus nurseries for the purpose of a possible license agreement, dated Jan. 9, 2014.

* cited by examiner

*Primary Examiner* — Kent L Bell
(74) *Attorney, Agent, or Firm* — Dentons US LLP

(57) ABSTRACT

'UFR-2' is a new and distinct allotetraploid *citrus* rootstock for tree size control and improved disease resistance. 'UFR-2' has shown a positive reaction to the Huanglongbing disease (HLB, or *citrus* greening disease) in multiple experimental field trials. Scion trees grafted on this rootstock show a reduced frequency of infection and reduced disease symptoms once infected as compared to commercial diploid rootstocks.

6 Drawing Sheets

BACKGROUND OF THE INVENTION

Latin name of the genus and species of the plant claimed: allotetraploid hybrid of [(*Citrus reticulata*×*Citrus paradisi*)+*Citrus grandis*]×[*Citrus reticulata*+*Poncirus trifoliata* (trifoliate orange)].

Variety denomination: 'UFR-2'.

The present invention relates to a new and distinct variety of *citrus* rootstock named 'UFR-2'. The Plant Improvement Team in Lake Alfred, Fla. has pioneered the development and testing of allotetraploid *citrus* rootstocks. 'UFR-2' (identified as Orange #4 in field trials) is an allotetraploid zygotic hybrid derived from a conventional cross of two somatic hybrids previously produced by protoplast fusion. The somatic hybrid seed parent is 'Nova' mandarin hybrid+'Hirado Buntan' pummelo (zygotic seedling), and the somatic hybrid pollen parent is 'Cleopatra' mandarin+'Argentine' trifoliate orange.

BRIEF SUMMARY OF THE INVENTION

'UFR-2' was selected as a potential *citrus* rootstock on the basis of its positive reaction to Huanglongbing disease (HLB, or *citrus* greening disease) in multiple experimental field trials. The claimed plant was first asexually reproduced by grafting to 'Swingle' citrumelo and 'Volkameriana' rootstocks and planted in Lake Alfred, Fla. The resulting trees were true to type. Scion trees grafted onto this rootstock showed a reduced frequency of infection and reduced disease symptoms once infected when compared to other commercial diploid rootstocks. 'UFR-2' is seedy and highly polyembryonic, making it amenable to standard nursery propagation practices for uniform liner production. Long-term performance of trees on this rootstock selection is unknown. Yield and fruit quality data is limited, but 3 years of data from young trees (the St. Helena project, see Table 1) indicates good productivity and fruit quality. Tolerance to *citrus* blight is also unknown, but under investigation.

TABLE 1

Rootstock Data from 5-year old trees in the St. Helena trial - Dundee, FL

| Scion | | Rootstock | Lbs Solids/Box 2012 | Lbs Solids/Box 2013 |
|---|---|---|---|---|
| 'VALQUARIUS' | Som. Hyb. | 'UFR-6' | 5.64 | 5.43 |
| 'VERNIA' | Som. Hyb. | 'UFR-6' | 5.67 | 6.01 |
| 'VALQUARIUS' | Tetrazyg | 'UFR-1' | 5.5 | 4.87 |
| 'VERNIA' | Tetrazyg | 'UFR-1' | 5.61 | 6.28 |
| 'VERNIA' | Tetrazyg | 'UFR-2' | 5.47 | 5.93 |
| 'VALQUARIUS' | Tetrazyg | 'UF'R-2' | 4.57 | 5.37 |
| 'VALQUARIUS' | Tetrazyg | 'UFR-3' | 4.84 | 5.05 |
| 'VERNIA' | Tetrazyg | 'UFR-3' | 5.46 | 5.82 |
| 'VERNIA' | Tetrazyg | 'UFR-4' | 5.79 | 6.07 |
| 'VALQUARIUS' | Tetrazyg | 'UFR-4' | 4.65 | 5.07 |
| 'VALQUARIUS' | Tetrazyg | 'UFR-5' | 5.76 | 5.72 |
| 'VERNIA' | Tetrazyg | 'UFR-5' | 5.89 | 5.34 |
| 'VALQUARIUS' | Diploid | 'FG 1731' | 5.83 | 6.81 |
| 'VALQUARIUS' | Diploid | 'FG 1731' | 5.12 | 5.63 |
| 'VERNIA' | Diploid | 'SWINGLE'* | 5.11 | 5.79 |
| 'VALQUARIUS' | Diploid | 'SWINGLE'* | NS | 5.61 |
| 'VERNIA' | Diploid | 'CLEO'* | 4.79 | 5.51 |
| 'VALQUARIUS' | Diploid | 'CLEO** | NS | 5.21 |
| 'VERNIA' | Diploid | 'R. LEMON'* | 3.67 | na |
| 'VALQUARIUS' | Diploid | 'VOLK'* | NS | 4.12 |
| 'VERNIA' | Diploid | 'VOLK'* | 3.6 | 4.73 |
| 'VALQUARIUS' | Diploid | 'KU-HARSKE'* | NS | 5.75 |
| 'VERNIA' | Diploid | 'KU-HARSKE'* | 4.34 | 5.83 |

| Scion | | Rootstock | Yield Boxes/Tree 2011 (35 mo.) | Yield Boxes/Tree 2012 (47 mo.) |
|---|---|---|---|---|
| 'VALQUARIUS' | Som. Hyb. | 'UFR-6' | 0.5 | 0.78 |
| 'VERNIA' | Som. Hyb. | 'UFR-6' | 0.4 | 0.63 |
| 'VALQUARIUS' | Tetrazyg | 'UFR-1' | NS | 0.72 |
| 'VERNIA' | Tetrazyg | 'UFR-1' | 0.31 | 0.67 |
| 'VERNIA' | Tetrazyg | 'UFR-2' | 0.35 | 0.25 |
| 'VALQUARIUS' | Tetrazyg | 'UF'R-2' | NS | 0.75 |
| 'VALQUARIUS' | Tetrazyg | 'UFR-3' | NS | 0.81 |
| 'VERNIA' | Tetrazyg | 'UFR-3' | 0.37 | 0.38 |
| 'VERNIA' | Tetrazyg | 'UFR-4' | 0.54 | 0.71 |
| 'VALQUARIUS' | Tetrazyg | 'UFR-4' | NS | 0.65 |
| 'VALQUARIUS' | Tetrazyg | 'UFR-5' | 0.33 | 0.56 |
| 'VERNIA' | Tetrazyg | 'UFR-5' | 0.42 | 0.25 |
| 'VALQUARIUS' | Diploid | 'FG 1731' | NS | 0.68 |
| 'VALQUARIUS' | Diploid | 'FG 1731' | NS | 0.67 |
| 'VERNIA' | Diploid | 'SWINGLE'* | 0.33 | 0.85 |
| 'VALQUARIUS' | Diploid | 'SWINGLE'* | NS | NS |
| 'VERNIA' | Diploid | 'CLEO'* | NS | 0.50 |
| 'VALQUARIUS' | Diploid | 'CLEO** | NS | NS |
| 'VERNIA' | Diploid | 'R. LEMON'* | NS | 0.78 |
| 'VALQUARIUS' | Diploid | 'VOLK'* | NS | NS |
| 'VERNIA' | Diploid | 'VOLK'* | 0.4 | 1.13 |
| 'VALQUARIUS' | Diploid | 'KU-HARSKE'* | NS | NS |
| 'VERNIA' | Diploid | 'KU-HARSKE'* | 0.15 | 0.75 |

TABLE 1-continued

Rootstock Data from 5-year old trees in the St. Helena trial - Dundee, FL

| Scion | | Rootstock | Yield Boxes/Tree 2013 (59 mo.) | Cumulative Yield (Boxes) |
|---|---|---|---|---|
| 'VALQUARIUS' | Som. Hyb. | 'UFR-6' | 1.94 | 3.22 |
| 'VERNIA' | Som. Hyb. | 'UFR-6' | 1.41 | 2.44 |
| 'VALQUARIUS' | Tetrazyg | 'UFR-1' | 2.23 | 2.95 |
| 'VERNIA' | Tetrazyg | 'UFR-1' | 1.33 | 2.31 |
| 'VERNIA' | Tetrazyg | 'UFR-2' | 1.38 | 1.98 |
| 'VALQUARIUS' | Tetrazyg | 'UF'R-2' | 1.73 | 2.48 |
| 'VALQUARIUS' | Tetrazyg | 'UFR-3' | 1.97 | 2.78 |
| 'VERNIA' | Tetrazyg | 'UFR-3' | 1.82 | 2.57 |
| 'VERNIA' | Tetrazyg | 'UFR-4' | 1.73 | 2.9S |
| 'VALQUARIUS' | Tetrazyg | 'UFR-4' | 1.59 | 2.64 |
| 'VALQUARIUS' | Tetrazyg | 'UFR-5' | 1.80 | 2.69 |
| 'VERNIA' | Tetrazyg | 'UFR-5' | 1.93 | 2.60 |
| 'VALQUARIUS' | Diploid | 'FG 1731' | 2.20 | 2.88 |
| 'VALQUARIUS' | Diploid | 'FG 1731' | 2.77 | 3.44 |
| 'VERNIA' | Diploid | 'SWINGLE'* | 1.08 | 2.26 |
| 'VALQUARIUS' | Diploid | 'SWINGLE'* | 1.50 | 1.50 |
| 'VERNIA' | Diploid | 'CLEO'* | 0.83 | 1.33 |
| 'VALQUARIUS' | Diploid | 'CLEO** | 1.7 | 1.7 |
| 'VERNIA' | Diploid | 'R. LEMON'* | na | 0.78 |
| 'VALQUARIUS' | Diploid | 'VOLK'* | 2.58 | 2.58 |
| 'VERNIA' | Diploid | 'VOLK'* | 0.83 | 2.36 |
| 'VALQUARIUS' | Diploid | 'KU-HARSKE'* | 2.2 | 2.2 |
| 'VERNIA' | Diploid | 'KU-HARSKE'* | 1.08 | 1.98 |

NS—not significanl fruit; na—data not available;
*control commercial rootstock
One box contains approximately 90 lbs. fruit.

BRIEF DESCRIPTION OF THE DRAWINGS

'UFR-2' is illustrated by the accompanying photographs, which show the tree's form, foliage, and fruit. The colors shown are as true as can be reasonably obtained by conventional photographic procedures. The photographs are of a tree approximately 6 years old. All figures were taken in the fall of 2013.

DETAILED BOTANICAL DESCRIPTION

Figure 1:
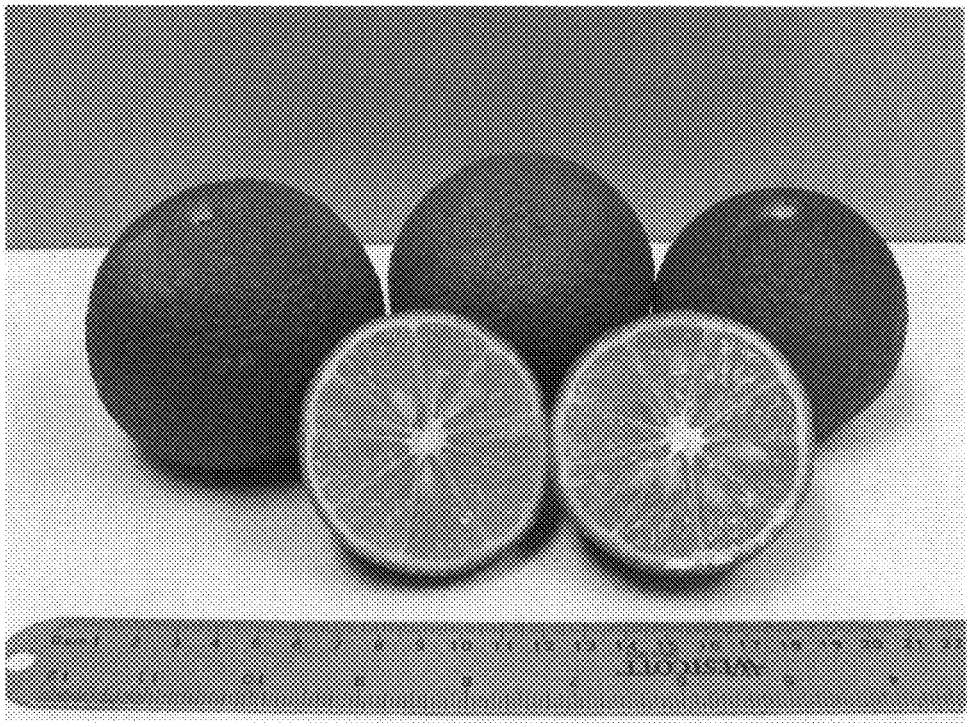
FIG. 1.—Shows a close-up of the nearly mature fruits with the rind and cross-sectional view of the fruit when cut in the center.
Figure 2:
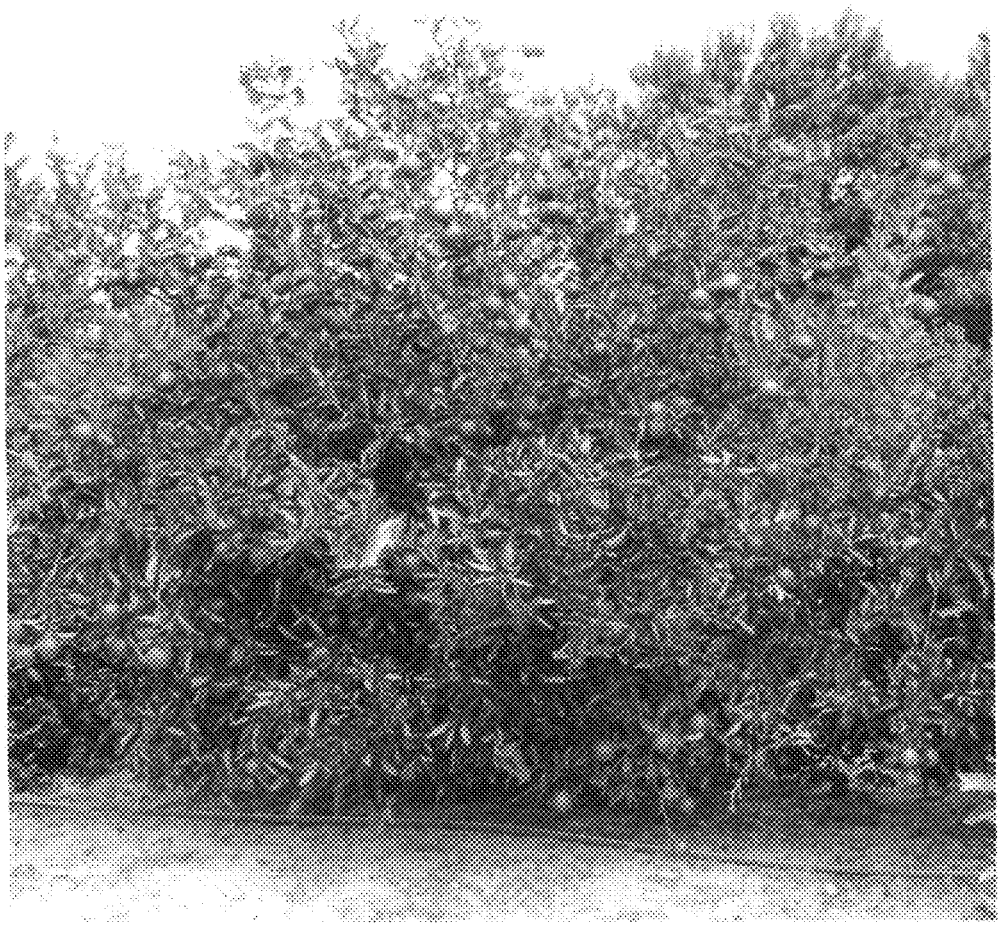
FIG. 2.—Shows the overall mature plant growth habit in October 2013.
Figure 3:
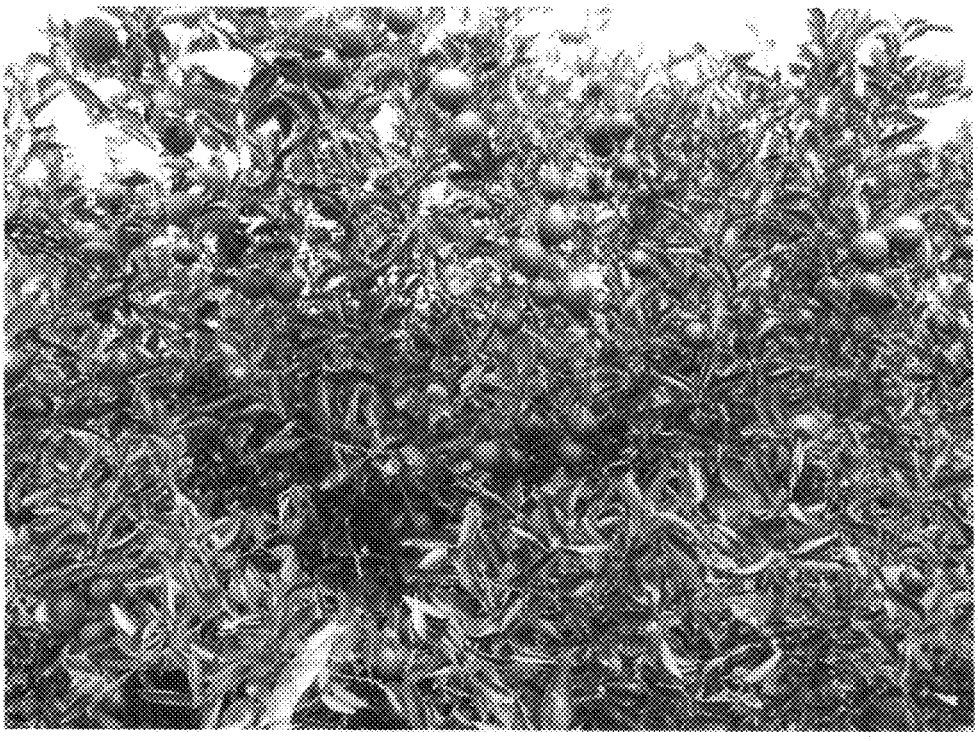
FIG. 3.—Shows nearly mature fruits hanging on the tree.
Figure 4:
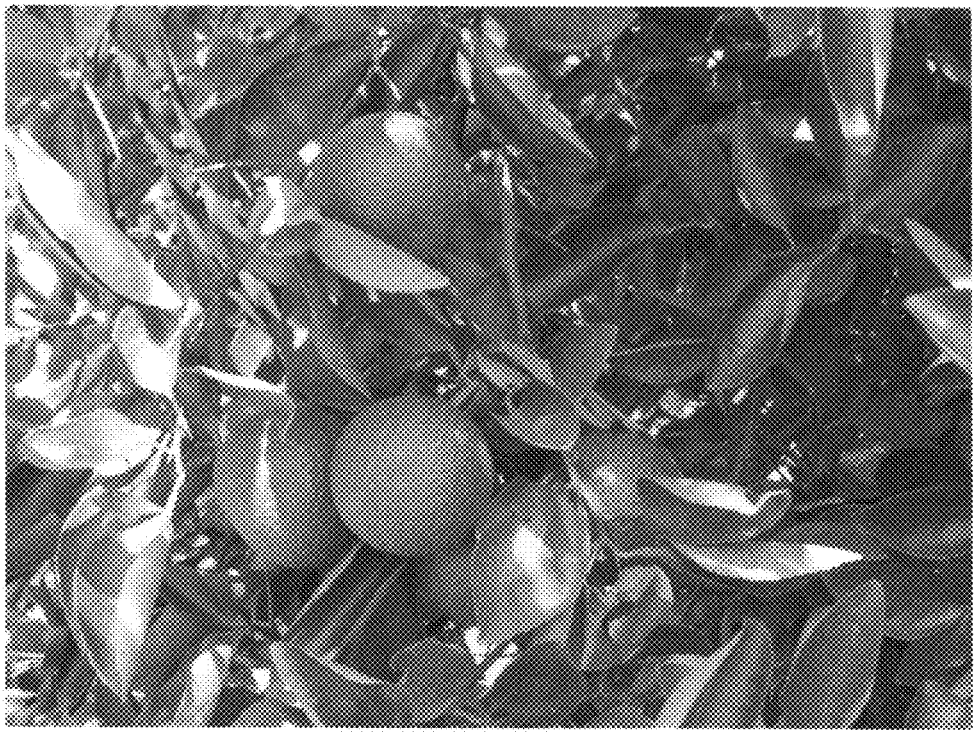
FIG. 4.—Shows a close-up of leaves and nearly mature fruits.
Figure 5:
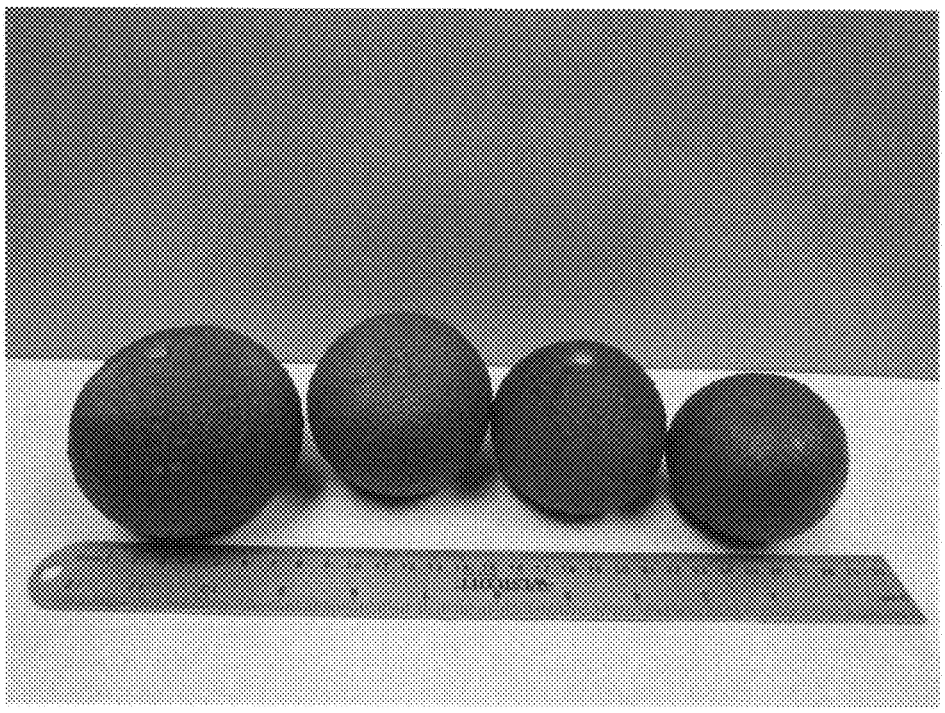
FIG. 5.—Shows a close-up of nearly mature fruits.
Figure 6:
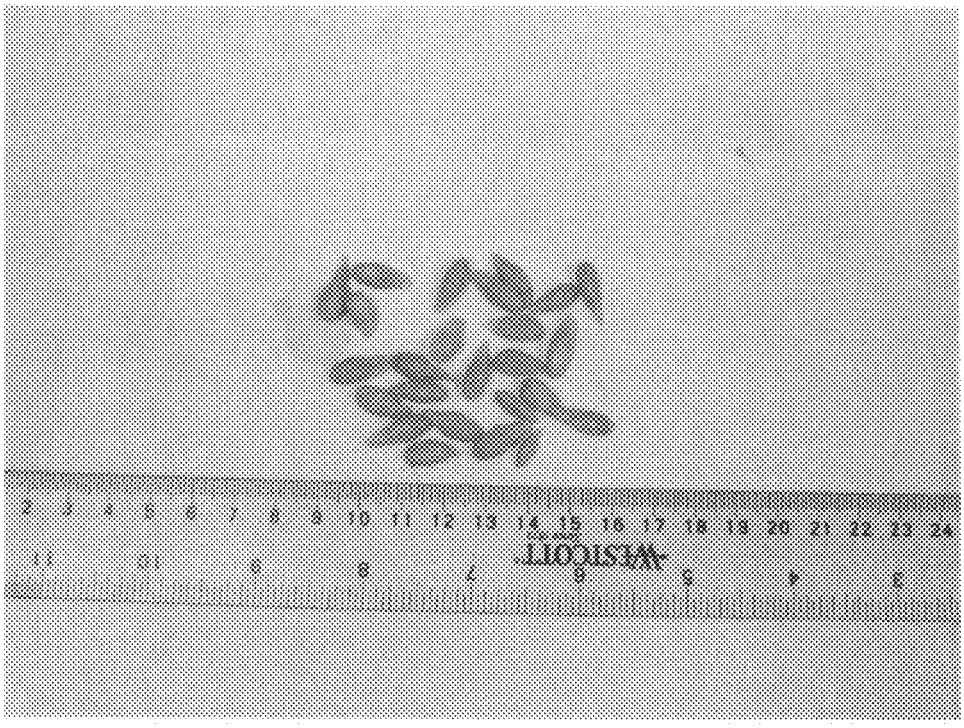
FIG. 6.—Shows a close-up of seeds from nearly mature fruit.

The following detailed description sets forth the distinctive characteristics of 'UFR-2'. The colors (except those in common terms) are described from R.H.S. Colour Chart published by The Royal Horticultural Society in London (second edition), in association with the Flower Council of Holland.

PHENOTYPIC DESCRIPTION OF *CITRUS RETICULATA* 'UFR-2'

Classification:

*Botanical.*—[*Citrus reticulata* hybrid ('Clementine' mandarin×'Orlando' tangelo) *Citrus reticulata*×*Citrus paradisi*)+*Citrus grandis*]×[*Citrus reticulata*+*Poncirus trifoliata* (trifoliate orange)].

*Common name.*—Complex allotetraploid 'tetrazyg' rootstock hybrid.

Parentage:

*Female parent.*—'Nova' mandarin+'Hirado Buntan' pummelo (zygotic seedling) somatic hybrid (unpatented).

*Male parent.*—'Cleopatra' mandarin+'Argentine' trifoliate orange; somatic hybrid (unpatented).

Tree:

*Ploidy.*—Tetraploid.

*Size.*—Medium.

*Height.*—3.2 meters.

*Tree spread.*—2.6 to 3.0 meters.

*Vigor.*—Vigorous.

*Density.*—Canopies are quite dense.

*Form.*—The tree has a round shape with mostly lateral branches growing toward low to medium angles. Branch with fruit exhibited drooping.

*Growth habit.*—Mostly lateral growth with upright growth on the top tree canopy.

Trunk:

*Trunk diameter.*—12 cm in diameter at 30 cm above the ground on a 6-year-old tree.

*Trunk texture.*—Smooth.

*Trunk bark color.*—RHS 198A (greyed-green); irregularly striated with RHS 143A (green).

Branches:

*Crotch angle.*—First crotch forms 15- to 20-degree angle, middle crotch forms an 80-degree angle.

*Branch length.*—Branch reaches 3.0 meters from the first crotch to the tip of the branch.

*Branch texture.*—Relatively rough with small thorns or spines.

*Branch color* (*shoots from previous flush, hardened and* 4 *to* 5 mm *in diameter*).—RHS N137A (green).

Leaves:

*Size* (*lamina average*).—Length: 89.9 mm. Width: 55.5 mm. L/W ratio: 1.6.

*Thickness.*—Thicker than average diploid *citrus* rootstock hybrids.

*Type.*—Mostly simple leaf types, occasionally with bifoliate and trifoliate types of leaves appearing within the same tree.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS N137A (green). Lower surface (abaxial): RHS 137C (green).

*Petiole.*—Shape: Brevipetiolate (shorter than leaf lamina); junction between petiole and lamina is articulate. Width (petiole wing): Narrow. Shape (petiole wing): Obovate. Length: 16.9 to 17 mm. Width: 3.9 to 4.0 mm. Color: RHS N137 (green).

Flowers and flower buds:

*Type.*—Hermaphrodite.

*Bearing.*—Flower grown from leaf axillaries and leaf terminals singly and in small clusters; most single flowers grow from leaf axillaries.

*Flower bud size.*—Shape: Initial visible flower bud has a round ball shape; mature flower bud has an elongated olive shape.

*Flower petals.*—Shape: Flat, spatula-shaped. Apex shape: Smooth, acute-shaped. Base shape: Even obtuse. Margin: Smooth.

*Flower sepal.*—Shape: Delta-shaped with an acute angle at the apex. Apex shape: Triangle-shaped. Margin: Smooth.

*Fragrance.*—Fragrant/Moderately fragrant.

*Reproductive organs.*—Fertility: Appears self-fertile. Pollen amount: Abundant/Moderate amount. Pollen color (general): Bright-yellow. Ovary shape: Oval-shaped.

Fruit:

*Size.*—Uniform.

*Height.*—59.2 to 73.2 mm on average.

*Width.*—67.4 to 80.5 mm on average.

*Average weight* (*per individual fruit*).—189.8 grams.

*Shape.*—Round.

*Shape* (*cross-section*).—Round.

*Apex.*—Truncated with slight dent.

*Apex cavity diameter.*—N/A.

*Base cavity diameter.*—7.0 to 7.1 mm.

*Base.*—No neck.

*Harvesting.*—Fruit can be harvested from October through December in Florida.

*Fruit stem* (*short stem connecting the fruit*).—Length: 5.0 mm. Diameter: 4.7 mm. Color: RHS 196A (greyed-green) with RHS 138A (green) strip.

Rind:

*Adherence.*—Adherence between albedo (mesocarp) and flesh (endocarp) is strong. The adherence is evenly distributed from base to apex.

*Thickness.*—3.4 to 3.8 mm on average.

*Texture.*—Smooth.

*Color.*—Flavedo (epicarp): Ranges between RHS 144B (yellow-green) to RHS 144A (yellow-green). Albedo (mesocarp): RHS 155A (white).

*Stylar end.*—Closed.

*Rind oil cell density.*—128 oil cells/square cm.

Flesh:

*Number of segments.*—Between 9 and 10 segments per fruit on average.

*Segment walls.*—Medium-firm with sufficient strength to maintain integrity as separated.

*Juice.*—Abundant.

*Color.*—Uniformly RHS 151D (yellow-green).

*Texture.*—Medium soft.

*Vesicles.*—Length: Arranged from 10.3 to 21.1 mm on average. Diameter (thickness): 1.5 to 2.9 mm on average.

*Eating quality.*—N/A.

*Juice index.*—

*Soluble solids* (*average*).—9 Brix.

Seeds:

*Type.*—Polyembryonic.

*Number.*—Ranges from 20 to 30. Most fruit contains less than 25 seeds.

*Shape*.—Seed shapes are not uniform. Normal seeds are mostly ventricose/swollen-shaped and clavate club shaped.

*Size*.—Length: 12.4 to 17 mm. Width: 4.8 to 6.0 mm.

*Seed coat color*.—Outer Surface: RHS 155C (white) and wrinkled. Inner surface: RHS 165C (greyed-orange). Cotyledon color: RHS 157B (green-white).

Resistance to disease: 'UFR-2' rootstock was selected on the basis of its positive reaction to HLB disease (huanglongbing or *citrus* greening disease) in multiple field trials. Trees on this rootstock show a reduced frequency of infection and reduced disease symptoms once infected as compared to commercial diploid rootstocks.

What is claimed is:

1. A new and distinct *citrus* rootstock plant as illustrated and described herein.

* * * * *